Dec. 9, 1958 P. ECKE Plant Pat. 1,779
POINSETTIA PLANT
Filed April 10, 1958
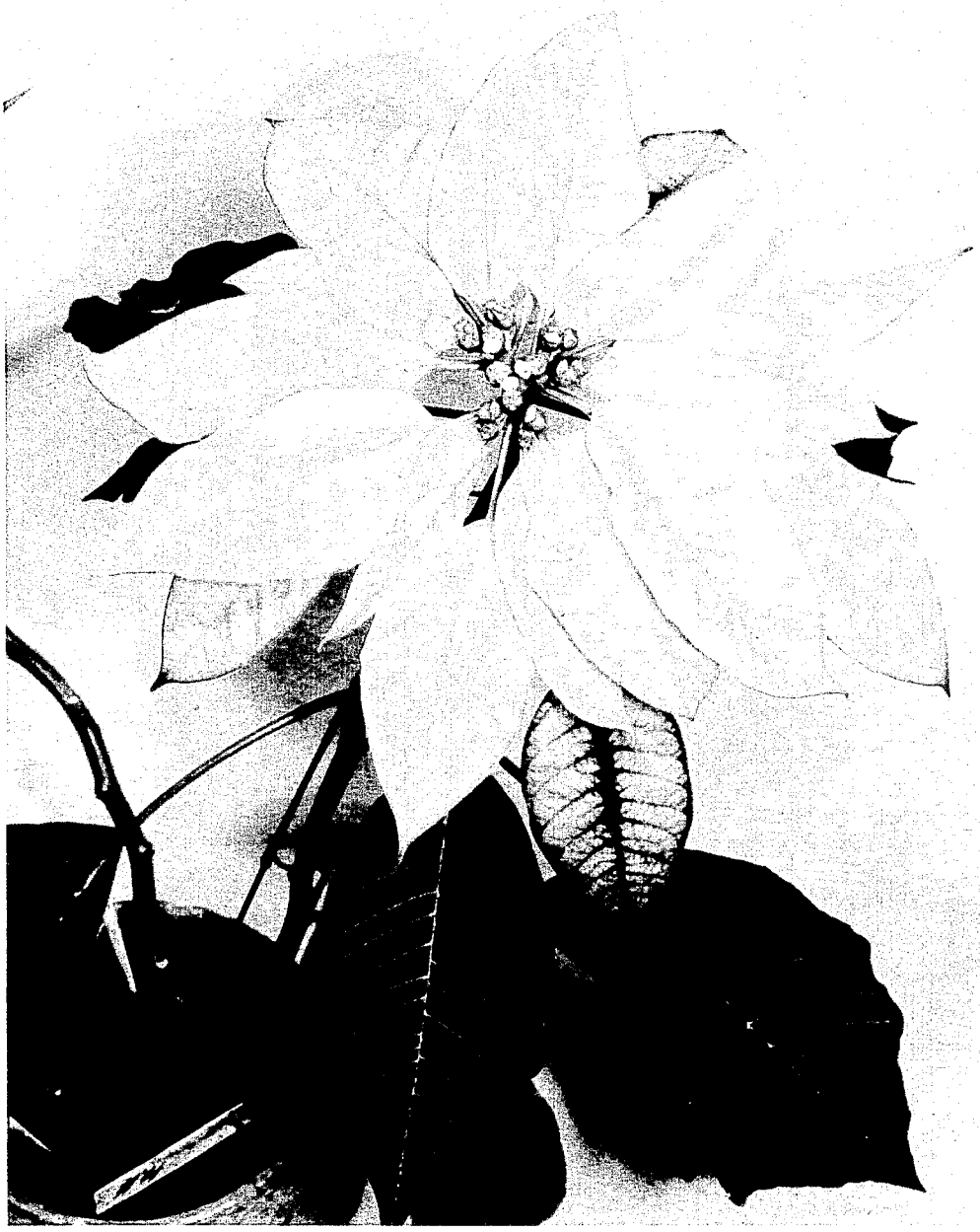
INVENTOR
Paul Ecke
by W. S. Graham
Attorney United States Patent Office Plant Pat. 1,779
Patented Dec. 9, 1958

1,779

POINSETTIA PLANT

Paul Ecke, Encinitas, Calif.

Application April 10, 1958, Serial No. 727,759

1 Claim. (Cl. 47—60)

The subject of the present invention or discovery is a new and distinct variety of poinsettia plant (*Euphorbia pulcherrima*) originating as a cultivated sport.

Broadly, this new variety of poinsettia plant is distinguishable from its parent plant, as well as from other known varieties, mainly in the shape, vivid pink-tinted red color and arrangement of the bracts, and its relatively late maturity, and to a lesser degree is distinguished by its rugged strong stalks or peduncles which ducing the height of plant growth.

The accompanying illustration, forming a part of this application, graphically shows in color this new variety, and more particularly its bracts involucre, inflorescence, portions of peduncle, and foliage leaves, at full maturity or optimum, the illustration being a face view of the subject showing its characteristics which differentiate this new variety.

The colors referred to herein correspond approximately with those shown in "Dictionary of Color" by Maerz and Paul (first edition, 1930), and more particularly identified by the color plate of said color standard by recapitulation in tabular form herein.

*Parentage*

This new variety was originated, discovered and cultivated by me in a cultivated area of a glass house or greenhouse at my experimental and growing gardens at Encinitas, San Diego County, California, and originating as a cultivated sport of poinsettia plant of the variety commonly known as "Ruth Ecke" poinsettia, which is patented in my Plant Patent No. 242, dated April 6, 1937, and well known in the trade by that name for many years and also referred to by that nomenclature in pertinent literature such as at page 508 of Florist Crop Production and Marketing by Kenneth Post, published 1949, New York, New York.

*Propagation*

This new variety of poinsettia plant has been asexually reproduced and cultivated by me in my greenhouse or glass house, located at Encinitas, San Diego County, California, by cuttings, and successive reproductions thereof have remained true to type and the characteristics herein described through asexual reproduction, cultivation and propagation through several generations, and its qualities and characteristics appear to be permanently fixed. In asexually reproducing this new variety I found it satisfactory and efficient to cut pieces of stalk of soft wood substantially six inches in length in the month of June, July and August, embedded one end of such cutitngs in beds of sand in my glass house, and after three or four weeks the cuttings are well rooted and may be transferred to individual pots. My experience has been that the optimum temperature for growing under glass is of the order of sixty to sixty-five degrees F., night temperature, the daytime temperature being warmer and subject to the varying conditions of light, heating, thickness of glass, cultivation, character of soil, fertilizer and pruning or pinching.

*Habits of growth*

This new variety of poinsettia is especially late in reaching the optimum of bract growth and coloration. Properly cultivated it will mature to optimum from December 10th to December 20th, which is approximately ten days later than usual red varieties, and therefore making this new variety especially desirable for the Christmas trade. It is also long-lasting, retaining bracts and leaf foliage for substantially two months, after which the plant will normally go dormant for about three months until the following spring.

*Structure*

The peduncles which branch from the main trunk are usually relatively short, stiff and very strong, and the internode space between foliage leaves is relatively short compared with other varieties, the normal result being that the height of the plant is lessened, as compared with its parent plant, its usual height being from four to five feet of luxurient wide bushy growth, its height and luxurient growth depending appreciably on the type of pruning or pinching, cultivation and fertilization, all of which have a tendency to cause a growth of side shoots which provide a luxurient wide body growth relatively shorter in height than the normal poinsettia plant. At the top or axial end of the peduncles a node is formed from which grow bract-bearing branches or stem-like spurs which bear the inflorescence and the bract involucre.

*Foliage leaves*

The foliage leaves are arranged around the peduncle, the nodes being more closely spaced than usual because of the relatively short internodes between joints. The foliage leaves are usually quite uniform in shape, and may be generally described as broad prolately-ovate, and pointed at the outer end, differing from the parent variety which has foliage leaves of the general oak-leaf type. The foliage leaves have relatively long petioles, and herringbone venation. The color of the foliage leaves may be broadly described as medium ivy green.

*Bracts*

The bracts, the rich color of which is a principal differentiating element of novelty of the present new variety, are firm and sufficiently thick to provide an opaqueness to their deep rich pink-tinted red color. They are formed in an involucre radiating from pale green bract-bearing branches, the majority of the petioles being relatively short, and the bracts being large, broad and numerous, thus providing a profusion of relatively large bracts which overlie relatively at adjacent edges in the nature of super-posed layers and forming an annular wreath, which because of the relatively short petioles is closely spaced to the inflorescence at its center.

The large bracts, in planar contour, are elongated and prolately ovate-acuminate; they are numerically greater in number of individual bracts than any of the known varieties of red poinsettias which have broad prolately ovate-acuminate bracts, the involucre having a predominating majority of the individual larger bracts of greater axial length and greater transverse width, greater thickness and greater individual planar area than known varieties of red poinsettias, thus providing an involucre of relatively wide diameter ranging up to six or seven inches.

At the optimum of their maturity the bracts may be generally and broadly described as a deep rich pink-tinted red color substantially uniform throughout the area of the bracts, and which by comparison is a deeper and more vivid red than the bracts of the parent variety (Plant Patent No. 242) or the variety of Plant Patent No. 1,068. The veining of the bracts is of the herring-bone type.

The petioles of the bracts are also of rich pink-tinted color, substantially similar to the color of the planar area of the bracts.

This new variety, being substantially ten days later in optimal maturity than other red varieties, reaches its optimum development of the bracts in a range of approximately December 10th to December 20th, and has excellent lasting qualities to about the middle of the following February, making the new variety a premium display plant close to and through the Christmas season which proverbially is the season for red and green decorative plants and more especially for poinsettia plants.

*Inflorescence*

A node is formed at the upper axial end of each main stalk or peduncle from which the bract-bearing branches or spurs grow upwardly and expansively apart, being usually three in number, and upon these branches or spurs grow a plurality of flower cyathia on short subacaulescent stems. Each cup-like cyathium is vase-like and contains a single pistillate flower surrounded by numerous staminate flowers, the pistillate flower pushing upward to the top where the stigma is spread for pollination. The cyathia are a pale green color and the flowers thereof are a lavender-red color. Alongside of the cyathia are the nectary or nectar cups the labial open mouth of which is of an orange-yellow color.

*Immunity*

The entire plant seems to be immune or highly resistant to disease and all other obnoxious and detrimental influences, and under such conditions its growth is strong and luxurient, rendering cultivation and propagation relatively easy under favorable conditions which are standard and normally exercised by those skilled in cultivation of poinsettia plants.

*Variations*

Different plants of this new variety have an unusual similarity of adherence to characteristics and type as herein described. However, there may be slight variations of minor detail in comparative growth of plants grown in various localities, in different soils, and at various times of the year, different temperatures, and whether grown in greenhouses or out of doors.

*Color tabulation*

The color designations according to the color plates of said "Dictionary of Color" are recapitulated in tabular form as follows:

| Part of Plant | Non-Technical Designation of Color | Plate | Letter | Number |
|---|---|---|---|---|
| Foliage leaves | Medium ivy green | 22 | L | 11 |
| Bracts | Pink-tinted red | 1 | L | 4 |
| Petioles of Bracts | do | 1 | L | 4 |
| Bract-bearing branches | Pale green | 21 | L | 3 |
| Inflorescence: | | | | |
| Flowers | Lavender-red | 49 | L | 3 |
| Cyathia | Pale green | 21 | L | 3 |
| Labials of nectar cups | Orange-yellow | 9 | L | 7 |

Having described and illustrated my new variety of poinsettia plant, I claim:

A new and distinct variety of poinsettia plant substantially as illustrated and described, characterized by an involucre of bracts which are prolately ovate-acuminate in plane, having a rich, pink-tinted red color, the bracts being sufficiently numerous to overlie in layers and sufficiently wide to overlap at adjacent edges, the petioles of the bracts being of a length to position the bracts relatively closely to an inflorescence centrally thereof, said new variety having the further characteristic of maturing to optimum substantially ten days later than known varieties of red poinsettias.

No references cited.